(12) United States Patent
Winkler

(10) Patent No.: US 8,641,653 B2
(45) Date of Patent: Feb. 4, 2014

(54) COMPRESSION GARMENT

(76) Inventor: Martin Winkler, Omaha, NE (US)

(*) Notice: Subject to any disclaimer, the term of this patent is extended or adjusted under 35 U.S.C. 154(b) by 0 days.

(21) Appl. No.: 13/223,111

(22) Filed: Aug. 31, 2011

(65) Prior Publication Data

US 2013/0014544 A1     Jan. 17, 2013

Related U.S. Application Data

(63) Continuation-in-part of application No. 11/063,114, filed on Feb. 22, 2005, now abandoned, and a continuation of application No. 12/291,654, filed on Nov. 12, 2008, now Pat. No. 8,034,013.

(51) Int. Cl.
     *A61F 13/00*      (2006.01)
(52) U.S. Cl.
     USPC ............................................... 602/60; 602/62
(58) Field of Classification Search
     USPC ............. 602/41–45, 60–65, 74–77, 900, 901; 66/147, 171, 195, 202
     See application file for complete search history.

(56) References Cited

U.S. PATENT DOCUMENTS

| | | | | |
|---|---|---|---|---|
| 3,306,288 A | * | 2/1967 | Rosenfield | 602/60 |
| 3,409,008 A | * | 11/1968 | Mortensen et al. | 602/76 |
| 3,570,482 A | * | 3/1971 | Emoto et al. | 602/76 |
| 3,728,875 A | * | 4/1973 | Hartigan et al. | 66/172 E |
| 3,747,374 A | * | 7/1973 | Meyer | 66/195 |
| 4,015,448 A | * | 4/1977 | Knohl | 66/185 |
| 4,377,160 A | * | 3/1983 | Romaine | 602/2 |
| 4,424,808 A | * | 1/1984 | Schafer et al. | 602/76 |
| 4,657,003 A | * | 4/1987 | Wirtz | 128/869 |
| 4,832,010 A | * | 5/1989 | Lerman | 602/63 |
| 5,257,956 A | * | 11/1993 | Ewen | 450/1 |
| 5,344,406 A | * | 9/1994 | Spooner | 604/179 |
| 5,695,452 A | * | 12/1997 | Grim et al. | 602/6 |
| 5,735,807 A | * | 4/1998 | Cropper | 602/63 |
| 6,311,334 B1 | * | 11/2001 | Reinhardt et al. | 2/239 |
| 6,435,221 B1 | * | 8/2002 | Waldrop et al. | 139/422 |

* cited by examiner

*Primary Examiner* — Kim M Lewis
(74) *Attorney, Agent, or Firm* — Merchant & Gould P.C.

(57) ABSTRACT

A compression garment comprises a plurality of longitudinal wales arranged to form a fabric having a length and generally parallel to the length, and a plurality of secondary transverse elastomeric threads connecting adjacent longitudinal wales and equally spaced about a length of the longitudinal wales. In a stretched state, the longitudinal wales are spaced from one another and remain generally parallel to the length.

16 Claims, 6 Drawing Sheets

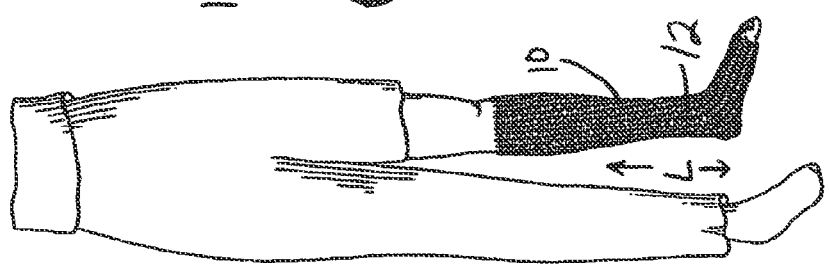
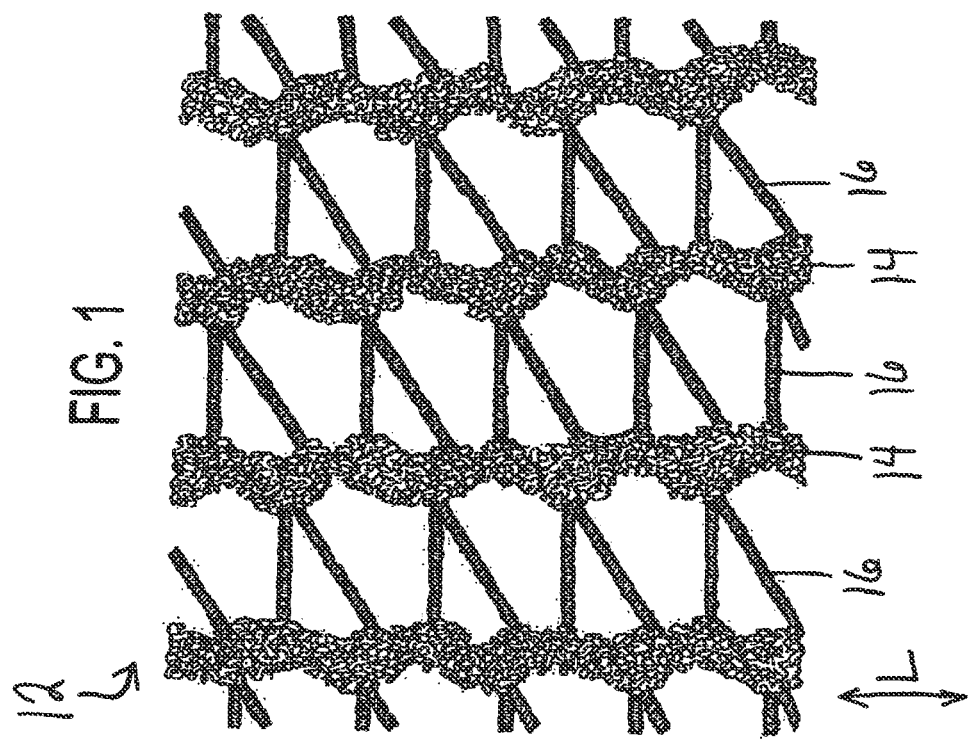

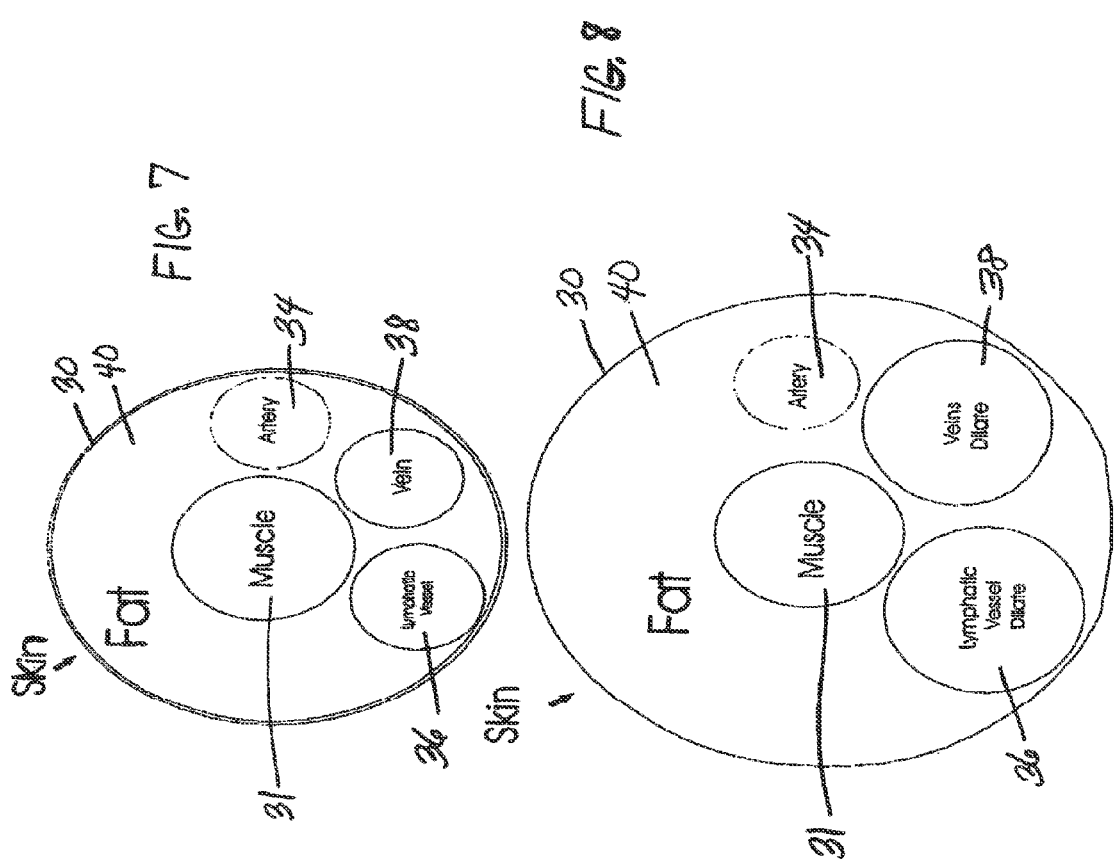

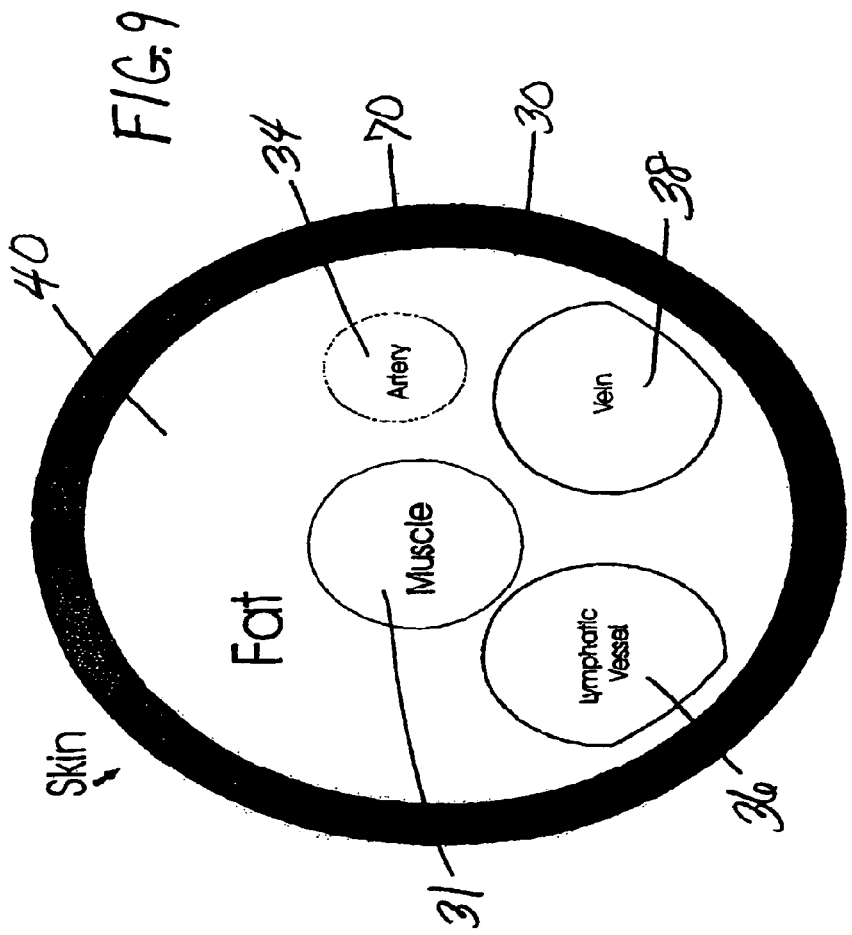

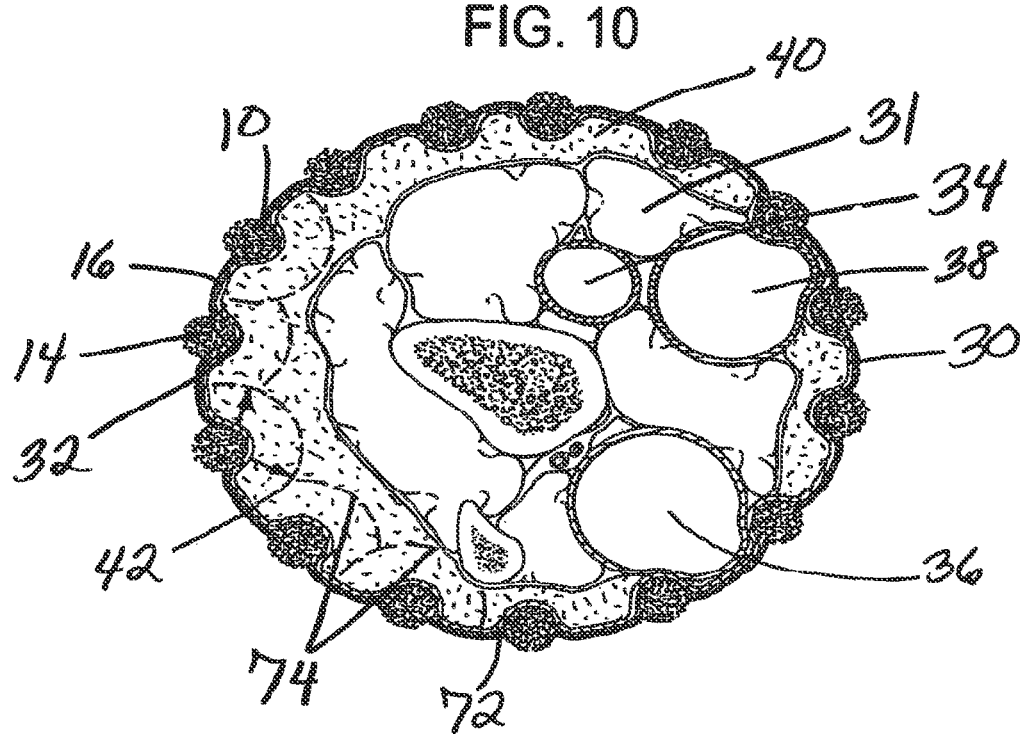

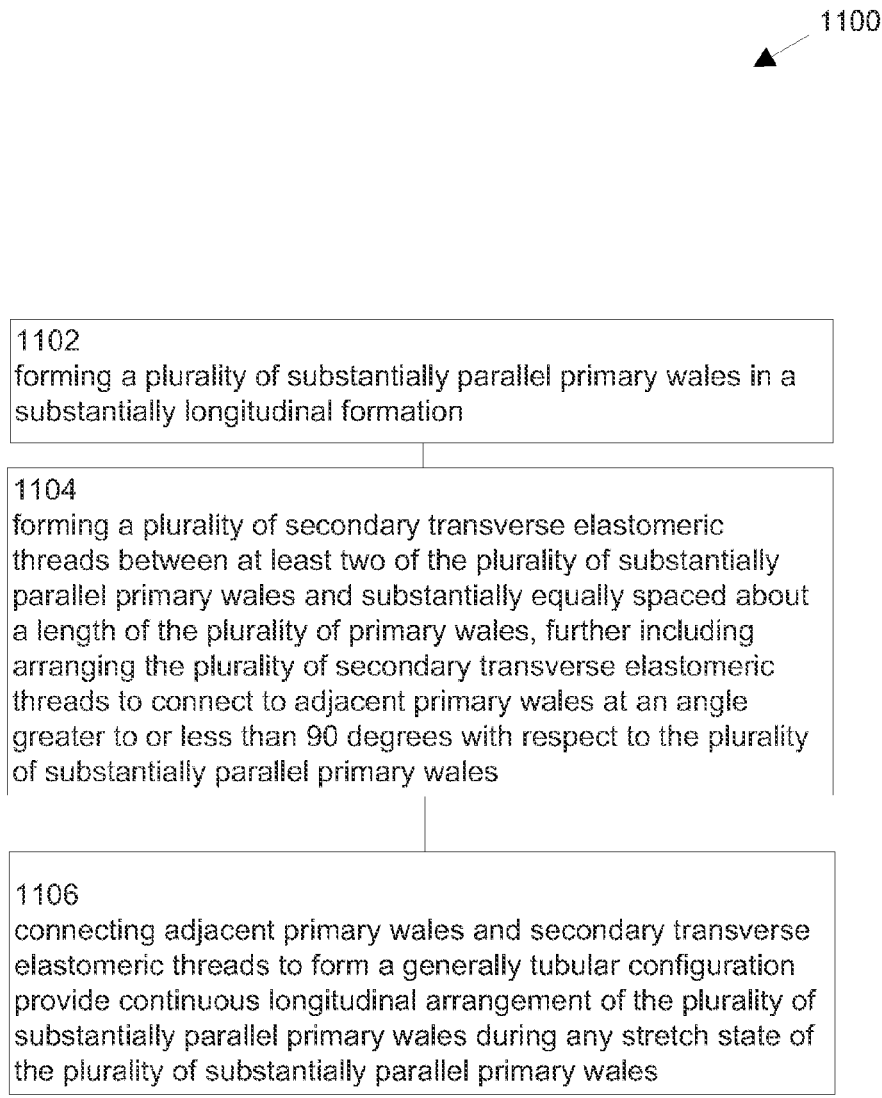

1102
forming a plurality of substantially parallel primary wales in a substantially longitudinal formation

1104
forming a plurality of secondary transverse elastomeric threads between at least two of the plurality of substantially parallel primary wales and substantially equally spaced about a length of the plurality of primary wales, further including arranging the plurality of secondary transverse elastomeric threads to connect to adjacent primary wales at an angle greater to or less than 90 degrees with respect to the plurality of substantially parallel primary wales

1106
connecting adjacent primary wales and secondary transverse elastomeric threads to form a generally tubular configuration provide continuous longitudinal arrangement of the plurality of substantially parallel primary wales during any stretch state of the plurality of substantially parallel primary wales

FIG. 11

COMPRESSION GARMENT

CROSS-REFERENCE TO RELATED APPLICATIONS

The present application is a continuation-in-part of and also claims the benefit of U.S. Non-Provisional application Ser. No. 11/063,114 filed Feb. 22, 2005 now abandoned. Said U.S. Non-Provisional application Ser. No. 11/063,114 filed Feb. 22, 2005 is hereby incorporated by reference in its entirety.

The present application is a continuation of and also claims the benefit of U.S. Non-Provisional application Ser. No. 12/291,654 filed Nov. 12, 2008 now U.S. Pat. No. 8,034,013. Said U.S. Non-Provisional application Ser. No. 12/291,654 filed Nov. 12, 2008 is hereby incorporated by reference in its entirety.

TECHNICAL FIELD

The invention relates to medical garments. More specifically, the invention relates to therapeutic compression garments.

BACKGROUND

Therapeutic garments and stockings are well known in the art and come in various configurations and are put to various uses. Compression therapy is primarily used for treating leg ulcers, treating dermatitis due to venous insufficiency (failure of veins and their valves to return blood to the heart), and treating congenital and acquired lymph edema and for treating edema due to congestive heart failure.

Known therapeutic compression garments and stockings are worn over the affected extremity and apply compression to the extremity which is generally evenly or smoothly distributed or applied to the surface area of the extremity. This compression assists the patient's venous return system in removing and returning blood from the extremity and towards the heart.

However, current therapeutic compression garments and stockings suffer from various drawbacks. One such drawback is that at any circumference along the length of the extremity, the known stockings apply a generally evenly distributed pressure about the limb. This relatively evenly distributed "pressure ring" tends to have a tourniquet effect on the limb which actually inhibits venous return. Also, known compressive stockings tend to slide more or less freely over the skin as the extremity to which the stocking is applied moves. This will occasionally produce a shearing injury to the skin. Shearing injury may also occur when the compression garment is put on or removed from the treated limb.

Additionally, prior art compression stockings are generally not well tolerated by patients as they tend to be uncomfortable, hot, cause excessive sweating of the underlying skin, all of which often limits the extent to which a patient may wear the prior art stocking.

The present invention is provided to solve the problems discussed above and other problems, and to provide advantages and aspects not provided by prior stockings of this type. A full discussion of the features and advantages of the present invention is deferred to the following detailed description, which proceeds with reference to the accompanying drawings.

SUMMARY

It is an aspect of one embodiment of the invention to provide a compression garment comprising a plurality of longitudinal wales arranged to form a fabric having a length and generally parallel to the length. The garment has a plurality of lateral elastomeric threads connecting adjacent longitudinal wales and equally spaced about a length of the longitudinal wales where, in a stretched state, the longitudinal wales are spaced from one another and remain generally parallel to the length. The longitudinal wales may have a fuzzy outer surface and/or a larger diameter than the lateral threads.

It is a further aspect of one embodiment of the invention to provide that when the garment is worn by a patient and in contact with and applying compression to a skin of the patient and in a stretched state such that each longitudinal wale is spaced from any adjacent longitudinal wale, each longitudinal wale presses into the skin and the skin stents each longitudinal wale by forming a longitudinal furrow in the skin that receives the longitudinal wale, the furrow tending to prevent relative movement of each longitudinal wale with respect to the skin.

In an additional embodiment of the disclosure, a device includes, but is not limited to, a plurality of substantially parallel primary wales in a substantially longitudinal formation; a plurality of secondary transverse elastomeric threads between at least two of the plurality of substantially parallel primary wales and substantially equally spaced about a length of the plurality of primary wales, the adjacent primary wales and secondary transverse elastomeric threads connected to form a generally tubular configuration, the plurality of secondary transverse elastomeric threads connected to adjacent primary wales at an angle greater to or less than 90 degrees with respect to the plurality of substantially parallel primary wales, and maintaining a continuous longitudinal arrangement of the plurality of substantially parallel primary wales during any stretch state of the plurality of substantially parallel primary wales.

In an additional embodiment of the disclosure, a method for forming a fabric includes, but is not limited to, forming a plurality of substantially parallel primary wales in a substantially longitudinal formation; forming a plurality of secondary transverse elastomeric threads between at least two of the plurality of substantially parallel primary wales and substantially equally spaced about a length of the plurality of primary wales, further including arranging the plurality of secondary transverse elastomeric threads to connect to adjacent primary wales at an angle greater to or less than 90 degrees with respect to the plurality of substantially parallel primary wales; and connecting adjacent primary wales and secondary transverse elastomeric threads to form a generally tubular configuration provide continuous longitudinal arrangement of the plurality of substantially parallel primary wales during any stretch state of the plurality of substantially parallel primary wales.

Other features and advantages of the invention will be apparent from the following specification taken in conjunction with the following drawings.

BRIEF DESCRIPTION OF THE DRAWINGS

To understand the present invention, it will now be described by way of example, with reference to the accompanying drawings in which:

FIG. 1 is a plan view of a fabric constructed according to the present invention in a stretched state;

FIG. 2 is a schematic showing a stocking made of the material of FIG. 1;

FIG. 3 is a schematic showing an elbow tube made of the material of FIG. 1;

FIG. 7 is a schematic of a patient's extremity in cross section in a "normal" state;

FIG. 8 is a schematic of a patient's extremity in cross section in a state of venous stasis disease;

FIG. 9 is a schematic similar to FIG. 8 showing the application of a prior art compression stocking;

FIG. 10 is a schematic similar to FIG. 8 showing the application of a compression garment according to the present invention; and FIG. 11 is a flow diagram illustrating a method for forming a compression garment according to an embodiment of the disclosure.

DETAILED DESCRIPTION

Figure 4:
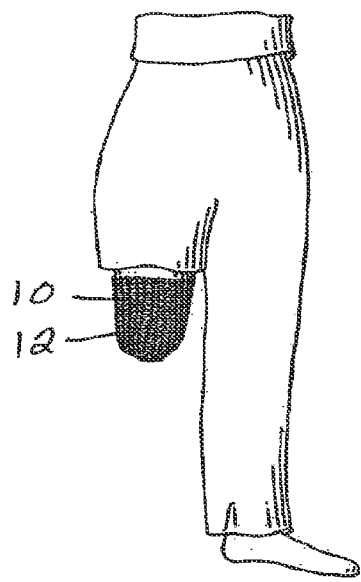
FIG. 4 is a schematic showing a stump tube made of the material of FIG. 1.

While this invention is susceptible of embodiments in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated.

FIG. 2 shows a therapeutic compression dressing or garment 10 according to the present invention having a generally tubular form. The fabric 12 from which the tubular compression garment 10 is formed is shown in more detail in FIG. 1. It can be seen that the fabric 12 includes a plurality of primary or longitudinal wales 14 and a plurality of secondary elastomeric threads 16. The primary wales 14 are arranged to be substantially parallel with a longitude L of the tubular compression garment 10. The secondary transverse elastomeric threads 16 extend between and connect adjacent primary wales 14, to be further described. The secondary transverse elastomeric threads 16 are arranged to be secondary to the longitude L. It can be seen that in the embodiment shown in the FIGS., the secondary transverse elastomeric threads 16 are arranged at an angle other than about 90 degrees to the longitude L.

The fabric 12 is knitted using a criss-crossing lateral stitch on a warp knitting machine. For instance, at least a portion of the plurality of substantially parallel primary wales and the plurality of secondary transverse elastomeric threads may be formed from a criss-crossing lateral stitch on a warp knitting machine to form the plurality of substantially parallel primary wales and the plurality of secondary transverse elastomeric threads. A resulting typical tube of fabric 12 includes 60 continuous longitudinal wales 14 connected by a plurality of secondary or lateral wales 16. Because of the six course repeat chain stitch that is used, when a tube of fabric 12 is stretched radially about any length of the fabric 12, the longitudinal wales 14 maintain their longitudinal orientation with respect to the overall tube of fabric 12. This is in contrast to other fabrics that may arguably include longitudinal wales and lateral elastomeric threads in an initial or relaxed state, wherein when stretched, the longitudinal wales 14 become arranged at an angle to the longitude of a tube made from the fabric.

In one preferred embodiment, and as shown, the primary or longitudinal wales 14 comprise a standard 3 ply 70 nylon wale having mild longitudinal recovery. One or more individual longitudinal wales 14 of the plurality of longitudinal wales 14 are fuzzy medical grade nylon knitted wales arranged to form a fabric cylinder having a length and generally parallel to the length. The longitudinal wale 14 is capable of being stretched between a first un-stretched length and a second or stretched position with a fully stretched length being approximately 350% longer than the unstretched length. Specifically, in a stretched state, (e.g., when deployed on a human extremity or torso of proper size), the longitudinal wales 14 may be spaced with a ratio of about four wale diameters between one another and remain generally parallel to the length.

The secondary transverse elastomeric threads 16 generate elastic compression in a starched state and are typically made from a polymer containing polyurethane such as commercially available spandex products. It is important to note that the diameter of each longitudinal wale 14 is significantly larger than the diameter of each secondary thread 16. Preferably, the diameter of the longitudinal wale 14 is approximately 11 times larger than the diameter of the secondary elastomeric spandex thread. The plurality of elastomeric threads may be elastomeric (e.g., spandex) or like elastic material and may connect adjacent longitudinal to form a fabric cylinder of longitudinal fuzzy wales equally spaced about a length of the longitudinal wale.

Figure 6:
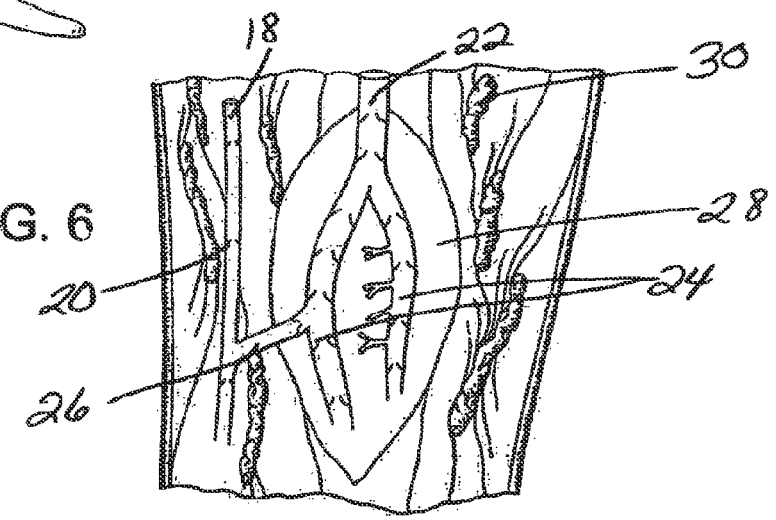
FIG. 6 is a partial schematic of a portion of a circulatory system of a patient.

Reference is now made to FIG. 6, which is a partial schematic of a portion of a circulatory system of a patient. FIG. 6 shows a schematic of a model of a venous pump in a patient's extremity, such as a leg. FIG. 6 shows a superficial vein 18 including various venous valves 20. Also shown is a popliteal vein 22 having a pair of depending deep crural trunks 24. The superficial vein 18 is connected to one of the deep crural trunks 24 by a perforator vein 26. The trunks 24 are surrounded by a musculofascial compartment 28. Interdispersed about all of the above are various fatty/cellulitic and connective tissues 30.

As discussed, known therapeutic compression garments apply a generally even or continuous pressure about the circumference of a patient's limb at any given point. Because of this fact, a patient is only able to tolerate a certain amount of compression at any one time, limiting the effectiveness of known garments Because of this limitation, most known garments only effect or assist primarily the superficial vein 18 in removing fluid from the affected area. Again, this limits the effectiveness of the garment.

A compression garment 10 made of fabric 12 according to the present invention, however, acts in a substantially different manner. Specifically, when a patient pulls on the compression garment 10, the fabric 12 stretches creating space between adjacent longitudinal wales 14. Because of the elastic nature of the lateral threads 16, each longitudinal wale 14 exerts a compression force on the skin or surface of the patient's limb, only at the point of contact between the longitudinal wale 14 and the skin. Actually, the "point of contact" is in fact a line of contact between the wale 14 and the skin, about the length of the longitudinal wale 14. Because of the disparity in the size of diameter of the primary wale 14 and the secondary elastomeric threads 16, the secondary, or lateral wales 16, do not exert any pressure directly on the limb in comparison to the pressure exerted by the longitudinal wales 14.

This has at least two effects. First the construction of the fabric 12 virtually eliminates any tourniquet effects obstructing the arterial, venous and lymphatic vessels in the subcutaneous fat found in prior art garments. Second, because in cross section, the longitudinal or linear compression exerted by the longitudinal wale 14 is felt by the limb at only discreet points about its circumference, it has been found that patients are much better able to tolerate higher compression forces. This, in turn, allows compression garments 10 constructed of fabric 12 according to the present invention to utilize greater pressures sufficient to assist the deeper popliteal vein 22 in also removing fluid from the affected area.

Figure 5:
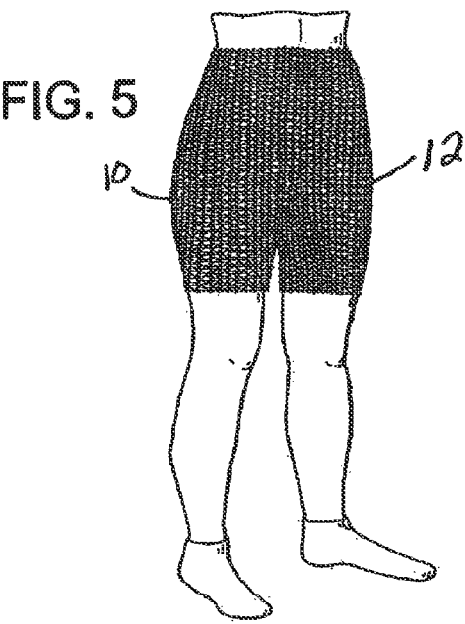
FIG. 5 is a schematic of a pair of shorts made of the material of FIG. 1.

As noted, the fabric 12 of the present invention may be used to create a tubular stocking to assist in treating the feet, ankles or any portion of the legs. The fabric 12 may also be used to form a sleeve (FIG. 3) for treating the knee or elbow area; or the fabric 12 may be used to form a closed end tube (FIG. 4) for treating and assisting in swelling reduction for stumps in amputation situations. Additionally, it has been found that the fabric 12 of the present invention is effective in treating and reducing the appearance of cellulite and therefore the fabric 12 may be used to form a pair of shorts (FIG. 5) extending down all or a portion of the thighs or a pair of tights (not shown) extending down the entirety of the legs.

It has been found that the fabric 12 of the present invention may be used to treat edema, runner's edema, arm and neck edema, deep venous thrombophlebitis, cellulite, or as a primary burn dressing or a skin graft first dressing. The fabric 12 may be formed into any shape necessary for treating any sort of swelling encountered in a patient whatsoever.

FIG. 7 shows a schematic cross section of a patient's extremity. Shown is an exterior layer of skin 30, muscle 31, an artery 34, a lymphatic vessel 36, a vein 38 and a subcutaneous fat layer 40. The lymphatic vessel 36 and the vein 38 are each involved in the removal or flow of fluid and blood out of the extremity. FIG. 7 shows the extremity in a normal state.

FIG. 8 shows the same extremity and elements in a diseased state. Particularly, the extremity of FIG. 8 is in a venous stasis diseased state. The subcutaneous fat layer 40 is swollen with various fluids including blood. Also, the lymphatic vessel 36 is dilated as is the vein 38. This is due, of course, to the fact that neither the lymphatic vessel 36 nor the vein 38 is operating properly.

FIG. 9 shows the same extremity and elements as originally shown in FIG. 8. However, a known prior art compression stocking 70 has been applied to the limb as represented by the thick bold line and the reference numeral 70. It can be seen that the prior art compression stocking 70 applies a consistent pressure to the extremity about the entirety of its outer surface. It can also be seen that the lymphatic vessel 36 and the vein 38 are slightly compressed.

FIG. 10 shows the same extremity as originally shown in FIG. 8. However, a compression garment 10 according to the present invention has been applied to the limb. As mentioned above and as further discussed below, the compression garment 10 applies pressure to the extremity at more discreet points along a circumference or outer layer of the extremity than does the prior art stocking 70, creating a scalloped effect 72 about the circumference of the extremity. The limb or extremity experiences more concentrated pressure directly under each primary or longitudinal wale 14. It can be seen that both the lymphatic vessel 36 and the vein 38 effectively experience or feel more compression with the compression garment 10 according to the present invention than they do with the prior art stocking 70 of FIG. 9.

The following is a discussion of the functionality of the present invention. The primary or longitudinal wale 14 alone is essentially in contact with the skin 30. Of course, the lateral elastomeric threads 16 also occasionally come into contact with the skin 30, but the lateral threads 16 do not exert any effective pressure on the extremity. The primary wales 14 have a soft or fuzzy outer surface. This fuzzy surface molds to the micro geography of the skin surface and "stents" the skin 30. Skin stenting will be further discussed below. The longitudinal fuzzy wale 14 stents the skin 30 holding the wale 14 in place over a small strip of skin cells. The longitudinal wales 14 do not move relative to furrows 32 of skin formed beneath the longitudinal wales 14, even with motion of the extremity. This prevents shearing injuries to the skin 30. The fact that skin shearing injuries do not occur with limb motion is a major improvement over older compression garments. Older compression garments, like that shown in FIG. 9, slide more or less freely over the skin 30 and occasionally produce shearing injuries. Shearing injuries also commonly occur with older compression garments when the tight garments are put on and removed.

The value of the "fuzzy" texture of the wale 14 is established in the medical industry. Natural "fuzzy" sheep fur, "sheep skins" and fuzzy synthetic "sheep skin" is a skin care industry standard. "Sheep skin" padding is used on beds, orthopedic appliances, and on wheel chair seats to prevent bed sores. The value of "fuzzy" textile material in contact with the skin 30 is known in the medical profession. The fabric 12 of the present invention brings the benefits of fuzzy wale skin stenting to compression therapy.

Additional value from the longitudinal fuzzy wale 14 includes its insulating properties. For instance, the plurality of substantially parallel primary wales may be formed from a material capable of raising the temperature of a region of skin in contact with the plurality of substantially parallel primary wales. In some instances, the longitudinal wale 14 insulates the skin 30 and generally raises the skin temperature one to three degrees F. It is known that elevating the skin temperature slightly can significantly increase blood flow to the feet of patients with arterial occlusive disease. Therefore, a compression garment 10 according the present invention tends to improve skin perfusion by warming the skin 30.

The longitudinal wales 14 in the fabric 12 of the present invention tends to create skin furrows 32 or "corn row furrows", as noted above, which can be seen in cross section in FIG. 10. The furrows 32 may reach a maximum depth of 1.5 to 2.0 times the radius of the longitudinal wale 14. The longitudinal wale 14 "presses in" and forms the furrows 32 in the skin 30. These furrows 32 provide significant benefit to the patient. The secondary or lateral elastomeric threads 16 transmit tension/compressive forces to the longitudinal wales 14. The longitudinal wales 14 are thereby "stented" in place by the skin 30 over a given small surface of skin 30. The longitudinal wales 14 focus compressive force on a small area of skin 30. Elastic compression presses the longitudinal wale 14 into the skin 30 and the furrows 32 form in the skin 30. The convex cross section of the longitudinal wale 14 acts to focus compressive force somewhat like the point of a nail, focusing the energy of a hammer blow onto a tiny surface, creating infinite pressure that drives the nail to pass through, for example, solid oak. Similarly, the skin 30 in the furrow 32 beneath the convex cross section of the longitudinal wale 14 experiences physiologically significant pressure.

The fuzzy outer surface of the wale may substantially stent and protect the skin in immediate contact with the fuzzy surface, creating a fuzzy skin nexus, while applying compression to the skin in contact with the fuzzy wale. Thus, when worn, a surface of a wearer's skin is in contact with a fuzzy skin nexus, and the fuzzy wale skin nexus applies a force of compression to the skin.

The secondary elastomeric fibers provide only the force of tension between wales. The secondary elastomeric fibers for the most part are not in functional contact with the skin. When in a state of tension, the secondary elastomeric fibers provide a skin surface geography with a ratio of compressed skin surface to substantially uncompressed skin surface of about one to five between adjacent longitudinal wales 14.

Under the force of elastomeric fiber tension, each longitudinal wale forms a longitudinal furrow in the skin that acts a biological stent. Specifically, under the force of the lateral elastomeric fiber tension, each longitudinal wale presses into the skin and the stents the skin. This compression of the skin forms a "corn row" furrow in the skin beneath the fuzzy nexus of each longitudinal wale. Also, under the force of elastomeric fiber tension, the longitudinal wale forming a longitudinal furrow in the skin tends to prevent relative movement of each longitudinal wale with respect to the skin.

Fixed fuzzy longitudinal wales 14 stretch the connected secondary spandex elastomeric threads. The elastomeric spandex fibers are substantially under only the force of tension and interact with the fuzzy longitudinal wales 14 which are substantially under only the force of compression. Secondary elastomeric (e.g., spandex) threads under tension between fixed fuzzy wales under compression create a tensegrity structure. This tensegrity structure, comprising a plurality of longitudinal wales 14, fixed in skin cornrow furrows, under the force of compression, and secondary elastomeric spandex threads, under only the force of tension, translates limb motion into changes in the length of the elastomeric components. Changes in elastic thread length changes the compression delivered to the skin via longitudinal wales resting in skin furrows . . . . Limb motion changes in the pressure of compression evidenced by the stented skin in cornrow furrows. Pressure changes in the sub cutaneous fat beneath the skin caused by motion of the wearer drives lymphatic pumping of lymph fluid.

The compression garment comprises a generally tubular stocking that has a "fuzzy nexus" with at least one fifth of the surface of the covered portion of a wearer's skin. That is, the 20 percent portion of the skin surface is under physiologically useful compression. Indentations, furrows, form in the 20 percent portion of the skin surface as a result of the force of compression. The compression garment also provides four fifths of the skin, between fuzzy wales, that is uncompressed. This uncompressed skin acts as a Sink for venous and lymphatic effluent drainage from the compressed skin, provides uncovered skin surface for evaporation of sweat, and provides uncovered skin surface for radiation of heat.

On a microscopic level, the following events occur in the skin beneath the longitudinal wale 14 in the furrow 32:

1.) The thin walled lymphatic vessels 36 (FIG. 10) in the fat 40 beneath the skin 30 are compressed and the lymph fluid in these vessels is pushed/squeezed/wrung out by the external pressure delivered by the longitudinal fuzzy longitudinal wale 14. Skin lymphatic vessels and skin veins have one way valves. Skin pressure changes in this valved tissue vascular structure produce a venous and a lymphatic "physiologic pump" that clears swelling from the skin and subcutaneous fat. Lymph fluid in healthy legs is pumped back to the heart from the feet with increased pressure gradients of 1 to 3 centimeters of water. Garments or dressings 10 created with the fabric 12 according to the present invention deliver a pressure to the sub dermal fat 40 in excess of 3 centimeters of water in a "halo" 74 of pressure that extends out from the skin furrow 32 beneath each longitudinal wale 14 and deeper into the fat 40 below the skin 30 than is possible with prior art compression devices. This halo 74 of pressure, from a cellular point of view, penetrates the fat 40 much deeper than pressure from older compression garments is able to penetrate. This halo 74 of pressure, exceeding three centimeters water, extends far into the tissue around the furrow 32. In this deeply penetrating halo 74 of high pressure, lymphatic flow is greatly enhanced.

2.) The thin walled veins 38 in the fat 40 beneath the longitudinal wales 14 are emptied of their fluid which constitutes deoxygenated blood rich in lactic acid. Veins 38 in the lower extremity may require pressure gradients of 5 to 15 centimeters of water to return fluid toward the heart. Garments or dressings 10 created with the fabric 12 according to the present invention may deliver pressure in excess of 15 centimeters of water in a halo 74 of high pressure around the longitudinal wale 14/skin furrow 32. The cells beneath the longitudinal wale 14 in the zone of pressure above 15 cm of water experience the following: perfusion by arterial blood in the capillaries; pressurized arterial blood is the only fluid that can enter the 74 of >15 centimeter/water tissue pressure. This halo 74 of >15 centimeter pressure causes rapid out flow of venous blood and lymphatic fluid, and causes elevated oxygen tension in the tissues. The halo 74 of >15 centimeter pressure penetrates the fat 40 much deeper than can pressure generated by older compression devices because the compressive energy is focused by the fluffy longitudinal wale 14 stent and the furrowing effect 32.

Furthermore, the oxygenated arterial blood in the capillaries beneath the skin furrows 32 allows for, in the subset of patients with chronic venous insufficiency, the "healing of venous stasis dermatitis." Venous stasis dermatitis occurs, in simple terms, because of oxygen starvation that occurs when fat 40 beneath the skin 30 is inundated by deoxygenated venous blood. Garments or dressings 10 created from the fabric 12 according to the present invention generate significant tissue pressures. The present invention focuses this pressure deep below the skin 30 and delivers pressure that may result in the skin 30 seeing approximately two to three times more tissue oxygen than with known compression devices. Physiologically, the tissue oxygen tension (PaO2) increases from approximately 30 to 38 Torr in venous stasis disease to 80 to 101 Torr when the present invention is utilized. The skin inflammation of venous stasis disease is called stasis dermatitis. Increased tissue oxygen pressure heals stasis dermatitis. Increased oxygen beneath the skin furrow 32 leads to cells being able to "repair" themselves. Redness disappears. Hair follicles begin to produce hair in areas under treatment. Skin ulcers heal. This healing of venous stasis ulcers with the present invention is dramatic when contrasted with older compression therapy devices. Older compression devices deliver compression to the entire surface of the extremity. Because of this, functional tissue pressure is ineffectively low in older compression devices.

The spaces between the longitudinal wales 14 are beneficial to the patient in at least five ways.

First, the spaces between the longitudinal wales 14 allow for evaporation of perspiration. Older compression garments can became wet with sweat. This trapped moisture can cause skin maceration. Macerated skin greatly increases the risk and potential for skin shear injuries and skin infection with bacteria or fungus.

Second, the spaces between longitudinal wales 14 allow for the radiation of body heat. Garments or dressings 10 produced with the fabric 12 according to the present invention remain cool and comfortable to wear in warm environments. Comfort enhances patient compliance. Older compression garments are extremely uncomfortable to wear in hot weather, making patient compliance poor.

Third, the spaces between the longitudinal wales 14 allow for the longitudinal wales 14 to press into the skin 30 creating the previously discussed skin furrows 32. The skin 30 between the furrows 32 is in a zone of no pressure 42. In the no pressure zone 42, the lymphatic 36 and the venous 38 vessels remain open. Lymphatic flow and venous flow can continue uninhibited toward the heart in the no pressure zone 42. Garments or dressings 10 produced with the fabric 12 according to the present invention do not create the tourniquet effect that is common in older compression garments. This tourniquet effect may be the greatest shortcoming of existing compression garments. The circumferential skin constriction of older compression devices blocks lymphatic and venous return to the heart. This tourniquet effect can actually contribute to the pathological condition that the older compression garment was prescribed to treat.

Fourth, the spaces between the longitudinal wales 14 allow for non-compressed skin 30 between the longitudinal wales 14/skin furrows 32. This non-compressed skin 30 allows the longitudinal wales 14 to focus a halo 74 of tissue compressive pressure deep into the fat 40 below the skin 30. The no pressure zone 42 enables the halo 74 of physiologically significant tissue pressure to deeply penetrate the fat 40 beneath the skin 30. Deep penetration encourages rapid tissue healing and rapid resolution of edema and other treatable conditions.

Fifth, when a garment or dressing 10 produced with the fabric 12 according to the present invention is removed for bathing (or other reasons) and replaced, the skin furrows 32 and the non-compressed skin 30 in the no pressure zones 42 are rearranged. This routine change in the location of the skin furrows 32 delivers therapeutic tissue compressive pressure to essentially all of the cells in the extremity roughly about 40% of the time. Thus, all of the cells in the skin 30 and the fat tissue 40 receive the benefit of high tissue pressures delivered in the halos 74 that penetrate deeply beneath the longitudinal wale 14 fibers. In older compression devices, the tissue pressure is constant, but low, to all areas of the skin 30 beneath the compression device.

The secondary or lateral elastomeric threads 16 of the present invention have at least five benefits.

First, the lateral threads 16 are (physiologically) not in contact with the skin 30. In some instances, the plurality of secondary transverse elastomeric threads are formed with an amount of space between at least two of plurality of secondary transverse elastomeric threads adequate to provide evaporation of perspiration and radiation of body heat. Thus, the lateral threads 16 may not prevent evaporation of perspiration, or trap body heat.

Second, the lateral threads 16 are not tightly woven in the fabric 12. There is less lateral wale 16 per unit area than in older compression garments. The lateral elastomeric threads 16 give or stretch easily. This easy stretching makes garments or dressings 10 produced with the fabric 12 of the present invention easy to put on and easy to remove. This increases patient compliance. No special jigs are required to put the garment on, such as is often required in older compression garments. Elderly, frail, patients with poor vision can remove and replace the compression garment 10 easily by simply pulling it on and off.

Third, the secondary or lateral elastomeric threads 16 help to prevent the risk of shearing injury to the skin 30. The fabric 12 of the present invention does not cause shearing injury to frail skin during the dangerous periods when compression garments are put on and removed. This is an improvement over older compression garments.

Fourth, the lateral secondary threads 16 are fixed in place between the longitudinal wales 14. The fluffy longitudinal wales 14 stent individual skin cells and the longitudinal wales 14 remain more or less stationary or in place during extremity motion. For instance, the plurality of secondary transverse elastomeric threads disposed between at least two of the plurality of substantially parallel primary wales and substantially equally spaced about a length of the plurality of primary wales may lengthen and shorten during extremity motion of a wearer and generate a dynamic change in tension translatable into a compressive force on the plurality of substantially parallel primary wales suitable for acting as a dynamic pump for at least one of a lymphatic vessel or a vein under a region of skin of a wearer. Extremity motion may transfer energy to the lateral threads 16 as the lateral threads 16 are stretched between the longitudinal wales 14. Extremity motion causes the lateral elastic threads 16 between the stationary longitudinal wales 14 to shorten and lengthen. This shortening and lengthening of the lateral threads 16 generates compressive force on the primary or longitudinal wales 14. This shortening and lengthening of the lateral wales 16 generates a dynamic compressive pressure experienced by the skin in furrows beneath the wales. This dynamic compressive pressure acts as an engine that translates extremity motion into compressive force and further acts as a dynamic pump for the lymphatic vessels 36 and the small veins 38 under the skin 30. With extremity motion, therefore, the present invention generates a dynamic change in tissue pressure that results in a pumping action in the veins 38 and the lymphatics 36 in the fat 40 beneath the skin 30.

Fifth, the lateral elastic threads 16 generate compressive forces that are focused by the longitudinal wales 14. Garments or dressings 10 made from the fabric 12 of the present invention have more "give" than traditional compression garments and are therefore more comfortable to wear than known compression garments. The patient does not have a "tight sensation." As garments or dressings 10 made according to the present invention are comfortable to wear, patient compliance is high. This "comfort factor" is in marked contrast to older compression garments that have an uncomfortable "tight squeeze" feel.

An externally treatable condition of a patient may be treated using the fabric 12. The method generally comprises the steps of providing a compression garment 10 comprised of the fabric 12 as described above, applying the compression garment 10 to an area of the patient having the externally treatable condition such that the compression garment 10 applies pressure to the area of the patient having the externally treatable condition, and removing the compression garment 10 from the area of the patient having the externally treatable condition after a period of time.

Referring to FIG. 11, a flow diagram illustrating a method 1100 for forming a compression garment according to an embodiment of the disclosure is shown. Method 1100 may be utilized to form embodiments of the compression garment as described above. In a preferred embodiment, the method 1100 for forming a fabric includes, but is not limited to forming a plurality of substantially parallel primary wales in a substantially longitudinal formation 1102, forming a plurality of secondary transverse elastomeric threads between at least two of the plurality of substantially parallel primary wales and substantially equally spaced about a length of the plurality of primary wales 1104, and connecting adjacent primary wales and secondary transverse elastomeric threads to form a generally tubular configuration provide continuous longitudinal arrangement of the plurality of substantially parallel primary wales during any stretch state of the plurality of substantially parallel primary wales 1106. The forming of the plurality of secondary transverse elastomeric threads between at least two of the plurality of substantially parallel primary wales and substantially equally spaced about a length of the plurality of primary wales further includes arranging the plurality of secondary transverse elastomeric threads to connect to adjacent primary wales at an angle greater to or less than 90 degrees with respect to the plurality of substantially parallel primary wales. The method may further include utilizing a criss-crossing lateral elastomeric stitch on a warp knitting machine to form the plurality of substantially parallel primary wales and the plurality of secondary transverse elastomeric threads. The forming a plurality of substantially parallel primary wales in a substantially longitudinal formation may further include forming the plurality of substantially parallel primary wales from a material having a diameter approximately 11 times larger than a diameter of a material utilized for forming the plurality of secondary elastomeric threads. The forming of a plurality of substantially parallel primary wales in a substantially longitudinal formation may further include forming the plurality of substantially parallel primary wales from a material having a fuzzy outer surface.

The forming of a plurality of substantially parallel primary wales in a substantially longitudinal formation may further include forming the plurality of substantially parallel primary wales from a material capable of raising the temperature of a region of skin in contact with the plurality of substantially parallel primary wales. The forming the plurality of substantially parallel primary wales from a material capable of raising the temperature of a region of skin in contact with the plurality of substantially parallel primary wales may further include forming the plurality of substantially parallel primary wales from a material capable of raising the temperature of a region of skin in contact with the plurality of substantially parallel primary wales approximately one to three degrees Fahrenheit.

The forming a plurality of secondary transverse elastomeric threads between at least two of the plurality of substantially parallel primary wales and substantially equally spaced about a length of the plurality of primary wales may further include forming the plurality of secondary transverse elastomeric threads from an elastomeric material.

The forming a plurality of secondary transverse elastomeric threads between at least two of the plurality of substantially parallel primary wales and substantially equally spaced about a length of the plurality of primary wales may further include forming an amount of space between at least two of plurality of secondary transverse elastomeric threads adequate to provide evaporation of perspiration and radiation of body heat. The forming a plurality of secondary transverse elastomeric threads between at least two of the plurality of substantially parallel primary wales and substantially equally spaced about a length of the plurality of primary wales may further include forming the plurality of secondary transverse elastomeric threads in a configuration fixing the plurality of secondary transverse elastomeric threads in place between the plurality of substantially parallel primary wales. The forming a plurality of secondary transverse elastomeric threads between at least two of the plurality of substantially parallel primary wales and substantially equally spaced about a length of the plurality of primary wales may further include forming the plurality of secondary transverse elastomeric threads between at least two of the plurality of substantially parallel primary wales and substantially equally spaced about a length of the plurality of primary wales from a material configured to lengthen and shorten during extremity motion of a wearer and generate a dynamic compressive pressure translatable into a compressive force on the plurality of substantially parallel primary wales. The forming the plurality of secondary transverse elastomeric threads between at least two of the plurality of substantially parallel primary wales and substantially equally spaced about a length of the plurality of primary wales from a material configured to lengthen and shorten during extremity motion of a wearer and generate a dynamic compressive pressure translatable into a compressive force on the plurality of substantially parallel primary wales may further include forming the plurality of secondary transverse elastomeric threads between at least two of the plurality of substantially parallel primary wales and substantially equally spaced about a length of the plurality of primary wales from a material configured to lengthen and shorten during extremity motion of a wearer and generate a dynamic compressive pressure translatable into a compressive force on the plurality of substantially parallel primary wales suitable for acting as a dynamic pump for at least one of a lymphatic vessel or a vein under a region of skin of a wearer.

The forming a plurality of secondary transverse elastomeric threads between at least two of the plurality of substantially parallel primary wales and substantially equally spaced about a length of the plurality of primary wales may further include forming an amount of space between at least two of the plurality of substantially parallel primary wales adequate to provide a pressure differential between a region of skin in contact with at least one of the plurality of substantially parallel primary wales and a region of skin covered by the plurality of secondary transverse elastomeric threads. The forming an amount of space between at least two of the plurality of substantially parallel primary wales configured to provide a pressure differential between a region of skin in contact with at least one of the plurality of substantially parallel primary wales and a region of skin covered by the plurality of secondary transverse elastomeric threads may further include forming an amount of space between at least two of the plurality of substantially parallel primary wales applying a non-therapeutic amount of pressure to a region of a wearer covered the plurality of secondary transverse elastomeric threads. The forming an amount of space between at least two of the plurality of substantially parallel primary wales adequate to provide a pressure differential between a region of skin in contact with at least one of the plurality of substantially parallel primary wales and a region of skin covered by the plurality of secondary transverse elastomeric threads may further include forming an amount of space between at least two of the plurality of substantially parallel primary wales adequate to create an amount of tension causing the plurality of substantially parallel primary wales to apply a substantially continuous amount of pressure to a region of a wearer covered by the plurality of substantially parallel primary wales.

The forming an amount of space between at least two of the plurality of substantially parallel primary wales adequate to provide an amount of compression causing the plurality of substantially parallel primary wales to apply a substantially continuous amount of pressure to a region of a wearer covered by the plurality of substantially parallel primary wales may further include forming an amount of space between at least two of the plurality of substantially parallel primary wales adequate to provide an amount of tension causing the plurality of substantially parallel primary wales to apply an amount of pressure sufficient to create a skin furrow within a region of a wearer covered by the plurality of substantially parallel primary wales.

It has been observed that the compression garments 10 constructed from the fabric 12 according to the present invention assist in treating at least the following conditions: any sort of edema including but not limited to edema resulting from prolonged periods of or repetitive exercise, resulting from high altitude exposure, or lymphedema from radiation therapy, or surgical disruption of lymph vessels, or lymphadenectomy for malignancy, or microfiliarial infestation lymph vessels, for example *Wuchereria bancrofti Brugia malayi*, and *B. timori*, or from venous insufficiency; skin ulcers due to venous insufficiency; venous stasis dermatitis; or muscle overuse syndrome, by increasing the ability of the lymphatic system to remove lactic acid and other toxic or inflammatory substances from the area of the muscle being exercised by the patient; enhanced healing of a repetitive use injury, including tennis elbow or other epicondylitis and shin splints (tibial compartment syndrome with periostitis) in runners; enhanced healing of skin graft donor site wounds; enhanced healing of split thickness skin grafts; enhanced healing of burn wounds of all degrees; enhanced hematoma absorption; swelling of any sort including that resulting from orthopedic or other injury; enhanced healing of surgical wounds, particularly in the extremities, including liposuction, vein stripping, and an injection of a sclerosing agent into a subcutaneous vein; treatment of cellulitis in soft tissue bacterial infections; enhanced recovery from ascending lymphangitis when used in concert with antibiotics; enhanced healing of neurotrophic dermatitis and enhances healing of neurotrophic ulcers of the lower extremity; enhanced treatment of extremity disuse edema such as may result from spinal chord injury and/or stroke; treatment of congenital edema; treatment of and improvement of cellulite including preventing or reducing its progression; and also enhances treatment of multiple skin conditions such as hives, uticaria and contact dermatitis.

Although the above descriptions and figures focus primarily on treating the extremities, wounds, swelling or any other condition described above that may be located on the torso, head or other area of the body may also be treated using the fabric 12 according to the present invention.

While the specific embodiments have been illustrated and described, numerous modifications come to mind without significantly departing from the spirit of the invention, and the scope of protection is only limited by the scope of the accompanying claims.

What is claimed:

1. A compression garment comprising:
    a plurality of longitudinal wales arranged to form a fabric having a length and generally parallel to the length; and
    a plurality of secondary elastomeric threads connecting adjacent longitudinal wales and equally spaced about a length of the longitudinal wales where, in a stretched state, the longitudinal wales are spaced from one another and remain generally parallel to the length, wherein the plurality of secondary elastomeric threads and the plurality of longitudinal wales are configured to provide an amount of space between the plurality of longitudinal wales creating an amount of tension to cause the plurality of longitudinal wales providing a substantially continuous longitudinal pressure zone for a region of skin in contact with the longitudinal wales and form a plurality of substantially parallel longitudinal furrows in the skin, and further provide a substantially no pressure zone in an adjacent region of the skin between the furrows covered by the plurality of secondary elastomeric threads.

2. The compression garment of claim 1, wherein the longitudinal wales have a fuzzy outer surface as the result of a specialized warp knitting process.

3. The compression garment of claim 1, wherein the longitudinal wales have a larger diameter than the secondary elastomeric threads.

4. A device comprising:
    a plurality of substantially parallel primary wales in a substantially longitudinal formation;
    a plurality of secondary transverse elastomeric threads between at least two of the plurality of substantially parallel primary wales and substantially equally spaced about a length of the plurality of primary wales, the substantially parallel primary wales and secondary transverse elastomeric threads connected to form a generally tubular configuration, the plurality of secondary transverse elastomeric threads connected to adjacent primary wales of the plurality of substantially parallel primary wales at an angle greater to or less than about 90 degrees with respect to the plurality of substantially parallel primary wales, and maintaining a continuous longitudinal arrangement of the plurality of substantially parallel primary wales during any stretch state of the plurality of substantially parallel primary wales, wherein the plurality of secondary elastomeric threads and the plurality of substantially parallel primary wales are configured to provide an amount of space between the plurality of substantially parallel primary wales adequate to create an amount of tension to cause the plurality of substantially parallel primary wales to provide a substantially continuous longitudinal pressure zone for a region of skin in contact with the substantially parallel primary wales and form a plurality of substantially parallel longitudinal furrows in the skin, and further provide a substantially no pressure zone in an adjacent region of the skin between the furrows covered by the plurality of secondary transverse elastomeric threads.

5. The device of claim 4, wherein the plurality of substantially parallel primary wales and the plurality of secondary transverse elastomeric threads are formed from a criss-crossing lateral stitch on a warp knitting machine to form the plurality of substantially parallel primary wales and the plurality of secondary transverse elastomeric threads.

6. The device of claim 4, wherein the plurality of substantially parallel primary wales in a substantially longitudinal formation further includes:
    a plurality of substantially parallel primary wales formed from a material having a diameter approximately 11 times larger than a diameter of a material utilized for forming the plurality of secondary transverse elastomeric threads.

7. The device of claim 4, wherein the plurality of substantially parallel primary wales are formed from a material having a fuzzy outer surface.

8. The device of claim 4, wherein the plurality of substantially parallel primary wales are formed from a material capable of raising the temperature of a region of skin in contact with the plurality of substantially parallel primary wales.

9. The device of claim 8, wherein the plurality of substantially parallel primary wales formed from a material capable of raising the temperature of a region of skin in contact with the plurality of substantially parallel primary wales further includes:
    a plurality of substantially parallel primary wales formed from a material capable of raising the temperature of a region of skin in contact with the plurality of substantially parallel primary wales approximately one to three degrees Fahrenheit.

10. The device of claim 4, wherein the plurality of secondary transverse elastomeric threads are formed from an elastomeric material.

11. The device of claim 4, wherein the plurality of secondary transverse elastomeric threads are formed with an amount of space between at least two plurality of the secondary transverse elastomeric threads adequate to provide evaporation of perspiration and radiation of body heat.

12. The device of claim 4, wherein the plurality of secondary transverse elastomeric threads are formed in a configuration fixing the plurality of secondary transverse elastomeric threads in place between adjacent substantially parallel primary wales.

13. The device of claim 4, wherein the plurality of secondary transverse elastomeric threads are formed from a material configured to lengthen and shorten during extremity motion of a wearer and generate a dynamic compressive pressure translatable into a compressive force on the plurality of substantially parallel primary wales.

14. The device of claim 13, wherein the plurality of secondary transverse elastomeric threads formed from a material configured to lengthen and shorten during extremity motion of a wearer and generate dynamic changes in elastomeric tension translatable into an elevated compressive force on the plurality of substantially parallel primary wales further includes:
   a plurality of secondary transverse elastomeric threads disposed between at least two of the plurality of substantially parallel primary wales and substantially equally spaced about a length of the plurality of primary wales formed from a material configured to lengthen and shorten during extremity motion of a wearer and generate a dynamic change in tension translatable into a compressive force on the plurality of substantially parallel primary wales suitable for acting as a dynamic pump for at least one of a lymphatic vessel or a vein under a region of skin of a wearer.

15. A method for forming a fabric comprises:
   forming a plurality of substantially parallel primary wales in a substantially longitudinal formation;
   forming a plurality of secondary transverse elastomeric threads between at least two of the plurality of substantially parallel primary wales and substantially equally spaced about a length of the plurality of primary wales, further including arranging the plurality of secondary transverse elastomeric threads to connect to adjacent primary wales at an angle greater to or less than about 90 degrees with respect to the plurality of substantially parallel primary wales; and
   connecting adjacent primary wales and secondary transverse elastomeric threads to form a generally tubular configuration provide continuous longitudinal arrangement of the plurality of substantially parallel primary wales during any stretch state of the plurality of substantially parallel primary wales, wherein the plurality of secondary elastomeric threads and the plurality of substantially parallel primary wales are configured to provide an amount of space between the plurality of substantially parallel primary wales adequate to create an amount of tension to cause the plurality of substantially parallel primary wales to provide a substantially continuous longitudinal pressure zone for a region of skin in contact with the substantially parallel primary wales and form a plurality of substantially parallel longitudinal furrows in the skin, and further provide a substantially no pressure zone in an adjacent region of the skin between the furrows covered by the plurality of secondary transverse elastomeric threads.

16. The method of claim 15, wherein the forming a plurality of secondary transverse elastomeric threads between at least two of the plurality of substantially parallel primary wales and substantially equally spaced about a length of the plurality of primary wales includes:
   forming the plurality of secondary transverse elastomeric threads in a configuration fixing the plurality of secondary transverse elastomeric threads in place between the plurality of substantially parallel primary wales.

\* \* \* \* \*